United States Patent
Arjavac et al.

(10) Patent No.: US 9,576,772 B1
(45) Date of Patent: Feb. 21, 2017

(54) CAD-ASSISTED TEM PREP RECIPE CREATION

(71) Applicant: FEI Company, Hillsboro, OR (US)

(72) Inventors: Jason Arjavac, Hillsboro, OR (US); Matthew P. Knowles, West Linn, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/868,056

(22) Filed: Sep. 28, 2015

Related U.S. Application Data

(60) Provisional application No. 62/212,352, filed on Aug. 31, 2015.

(51) Int. Cl.
*H01J 37/304* (2006.01)
*G01N 1/28* (2006.01)

(52) U.S. Cl.
CPC ............ *H01J 37/3045* (2013.01); *G01N 1/28* (2013.01); *H01J 2237/31732* (2013.01); *H01J 2237/31745* (2013.01)

(58) Field of Classification Search
None
See application file for complete search history.

(56) References Cited

U.S. PATENT DOCUMENTS

| | | | | |
|---|---|---|---|---|
| 5,604,819 A | * | 2/1997 | Barnard | G06T 5/20 382/151 |
| 6,670,610 B2 | * | 12/2003 | Shemesh | H01J 37/304 850/9 |
| 7,570,796 B2 | * | 8/2009 | Zafar | G03F 1/84 382/144 |
| 8,134,124 B2 | | 3/2012 | Blackwood et al. | |
| 8,890,064 B2 | | 11/2014 | Arjavac et al. | |
| 2015/0136977 A1 | | 5/2015 | Buxbaum | |

* cited by examiner

*Primary Examiner* — Jack Berman
(74) *Attorney, Agent, or Firm* — Scheinberg & Associates, P.C.; Michael O. Scheinberg

(57) ABSTRACT

An improved process workflow and apparatus for S/TEM sample preparation and analysis is provided. Preferred embodiments provide improved methods for an automated recipe TEM sample creation, especially for small geometry TEM lamellae, employing CAD data to automatically align various stages of sample preparation. The process automatically verifies and aligns the position of FIB-created fiducials by masking off portions of acquired images, and then comparing them to synthesized images from CAD data. SEM beam positions are verified by comparison to images synthesized from CAD data. FIB beam position is also verified by comparison to already-aligned SEM images, or by synthesizing an FIB image from CAD using techniques for simulating FIB images. The automatic alignment techniques herein allow creation of sample lamellas at specified locations without operator intervention.

15 Claims, 10 Drawing Sheets

CAD-ASSISTED TEM PREP RECIPE CREATION

CROSS-REFERENCE TO RELATED APPLICATIONS

This Application claims priority from U.S. Provisional Application 62/212,352, filed Aug. 31, 2015, which is hereby incorporated by reference.

TECHNICAL FIELD

The present invention relates to sample preparation workflows with charged particle beam devices, and in particular toward highly automated recipes for preparing transmission electron microscope samples.

BACKGROUND OF THE INVENTION

Features on semiconductor wafers and dies are three-dimensional structures and a complete characterization must describe not just a surface dimension, such as the top width of a line or trench, but a complete three-dimensional profile of the feature. Process engineers must be able to accurately measure the critical dimensions (CD) of such surface features to fine tune the fabrication process and assure a desired device geometry is obtained.

Typically, such CD measurements are made using instruments such as a scanning electron microscope (SEM). In a scanning electron microscope (SEM), a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features continue to get smaller and smaller, however, there comes a point where the features to be measured are too small for the resolution provided by an ordinary SEM.

As semiconductor geometries continue to shrink, manufacturers increasingly rely on transmission electron microscopes (TEMs) for monitoring the process, analyzing defects, and investigating interface layer morphology. TEMs allow observers to see features having sizes on the order of nanometers, and to see the internal structure of a sample. The sample must be sufficiently thin to allow many of the electrons in the primary beam to travel though the sample and exit on the opposite site.

Because a sample must be very thin for viewing with transmission electron microscopy (whether TEM or STEM), preparation of the sample can be delicate, time-consuming work. The term "TEM" as used herein refers to a TEM or a STEM and references to preparing a sample for a TEM are to be understood to also include preparing a sample for viewing on an STEM. TEM samples are typically less than 100 nm thick, but for some applications samples must be considerably thinner. With advanced processes at 30 nm, 22 nm, and below, the sample needs to be less than 20 nm in thickness in order to avoid overlap among small scale structures. The precision and accuracy involved in producing such samples is typically very time consuming. In fact, even though the information that can be discovered by TEM analysis can be very valuable, the entire process of creating and measuring TEM samples has historically been so labor intensive and time consuming that it has not been practical to use this type of analysis for manufacturing process control. While the use of focused ion beam (FIB) methods in sample preparation has reduced the time required to prepare samples for TEM analysis down to only a few hours, it is not unusual to analyze 15 to 50 TEM samples from a given wafer. As a result, speed of sample preparation is a very important factor in the use of TEM analysis, especially for semiconductor process control.

FIG. 4 illustrates a prior art automated S/TEM sample management (available commercially as the ExSolve™ system) according to described in U.S. Pat. No. 8,890,064 to Arjavac et al. The ExSolve wafer TEM prep (WTP) workflow addresses the needs of facilities that require automated, high-throughput sampling at advanced technology nodes. It complements the capabilities of dual beam systems such as the FEI company's Helios NanoLab™ DualBeam™ 1200AT, which provides more flexible, operator-directed, sample preparation methods, along with additional capabilities such as high-resolution scanning electron microscopy (SEM) imaging and analysis.

In the depicted system of FIG. 4, TEM samples are processed by a cluster of different processing tools having the capability of sequentially processing samples (e.g., lamellae extracted from semiconductor wafers). The S/TEM sample management tool suite 100 generally includes a Process Controller 110 and a Fab Host computer 112 operably connected to (or integrated with) a FIB system 114, a lamella extraction tool 116 such as an Ex-Situ Plucker ("ESP"), and a S/TEM system 118. FIB system 114 may comprise a dual beam FIB/SEM system such as the Certus™/CLM available from FEI Company of Hillsboro, Oreg., the assignee of the present invention; and S/TEM system 118 may comprise a system such as a Tecnai™ G2 S/TEM also available from FEI Company. In the system of FIG. 4, each processing tool is operably connected to (or integrated with) a computer station 120, which uses software 122 for implementing TEM sample creation and processing. Any suitable software (conventional and/or self-generated) applications, modules, and components may be used for implementing software. For example, in the system of FIG. 4, the automated S/TEM sample management is implemented using IC3D™ software for automated machine control and metrology, which is also available from FEI Company.

However, even in such automated systems, the requirement for manual intervention at various recipe creation steps such as specifying and verifying fiducial locations slows down the process. The time and number of representative samples required to develop/create a fully automated TEM sample preparation recipe (or "TEM prep recipe") is too long to enable leading semiconductor manufacturers to realize "time to data" in an automated workflow for both process monitoring and defect root cause analysis. Foundry-type manufactures are specifically challenged due to the large number of different wafers for different fabless customers. By the time they develop a robust recipe, the pattern may have changed so a new recipe would have to be developed. Recipe development time must be reduced and optimally automated to enable foundry customers to realize the benefits of fully automated TEM Prep.

For TEM prep, the problem is presently solved by skilled engineers creating the recipe in an advanced visual scripting authoring software framework that enables automation of a wide range of instrument control commands and imaging tasks (the iFAST™ software by FEI) software on an automated, high-throughput sample preparation system that can prepare site-specific lamellae (the ExSolve™ system described briefly above), creating test samples, and manually analyzing samples in offline TEM. The learning is then applied to the recipe parameters and the process is iterated. However, such a process is relatively slow and resource intensive, and not readily scalable. Recipe creation/development for a fully automated TEM prep processing can be a time consuming and applications engineering intensive activity due to lack of pre-determined knowledge of pattern information available on wafer/sample.

SUMMARY OF THE INVENTION

The present invention provides a solution to this problem by linking CAD, or primary circuit/layout design data to multiple steps of the recipe creating a corrected feedback for beam positioning to ensure accurate placement of beam for lamella processing. The CAD helps automate and speed the TEM prep in an automated, stepwise methodology. An improved process workflow and apparatus for S/TEM sample preparation and analysis is provided. Preferred embodiments provide improved methods for an automated recipe TEM sample creation, especially for small geometry TEM lamellae, employing CAD data to automatically align various stages of sample preparation. The process automatically verifies and aligns the position of FIB-created fiducials by masking off portions of acquired images, and then comparing them to synthesized images from CAD data. SEM beam positions are verified by comparison to images synthesized from CAD data. FIB beam position is also verified by comparison to already-aligned SEM images, or by synthesizing an FIB image from CAD using techniques for simulating FIB images. The automatic alignment techniques herein allow creation of sample lamellas at specified locations without operator intervention.

One embodiment provides a method for automatically preparing a semiconductor sample in a dual-beam charged particle system. The method includes positioning the dual-beam charged particle system with respect to a semiconductor die sample region of interest to be examined in a sample chamber. With focused ion beam (FIB) deposition, the method creates a first precision fiducial marker and one or more additional fiducial markers at desired locations with respect to the region of interest. The fiducial may be created by deposition or milling, but in preferred embodiments is created with deposition. Then the position of the fiducials is verified and aligned by acquiring a first scanning electronic microscope (SEM) image of the region of interest, retrieving computer aided design (CAD) data describing the region of interest, synthesizing a second SEM image from CAD data describing the region of interest, masking the one or more additional fiducial markers in the first SEM image, and comparing the masked first SEM image and the second SEM image to determine a final correction offset for an actual position of the precision fiducial marker. The final correction offset is applied to the tracked location of the precision fiducial marker. Then, based on the corrected location of the precision fiducial marker, the process adjusts the position of the FIB relative to the FIB, and mills with the FIB to create a sample lamellae for examination. The steps may be performed at multiple specified locations to create multiple lamellas from a sample wafer or device.

The invention also includes systems with automated controllers and program products executable to conduct the automated workflow processes herein. For example, some embodiments provide an automated sample preparation system including a dual-beam scanning and milling system with a scanning electron microscope (SEM), a focused ion beam (FIB) both pointing at a sample chamber, a system controller operatively connected to the SEM and FIB and including at least one processor and tangible non-transitory computer media storing program instructions executable by the at least one processor for controlling the dual beam scanning and milling device to conduct the processes described above. The dual beam system may also be integrated into a larger sample management suite with automated sample handling, including a plucker device operable to remove one or more lamellas from the sample, a transmission electron microscope (TEM), operable to receive the one or more lamellas from the plucker device and conduct scans, and a process controller operatively connected to the dual beam scanning and milling system, the plucker device, and the TEM and operable to command them to execute functions in an automated workflow.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions and the accompanying drawings, in which.

DETAILED DESCRIPTION OF PREFERRED EMBODIMENTS

Figure 1A:
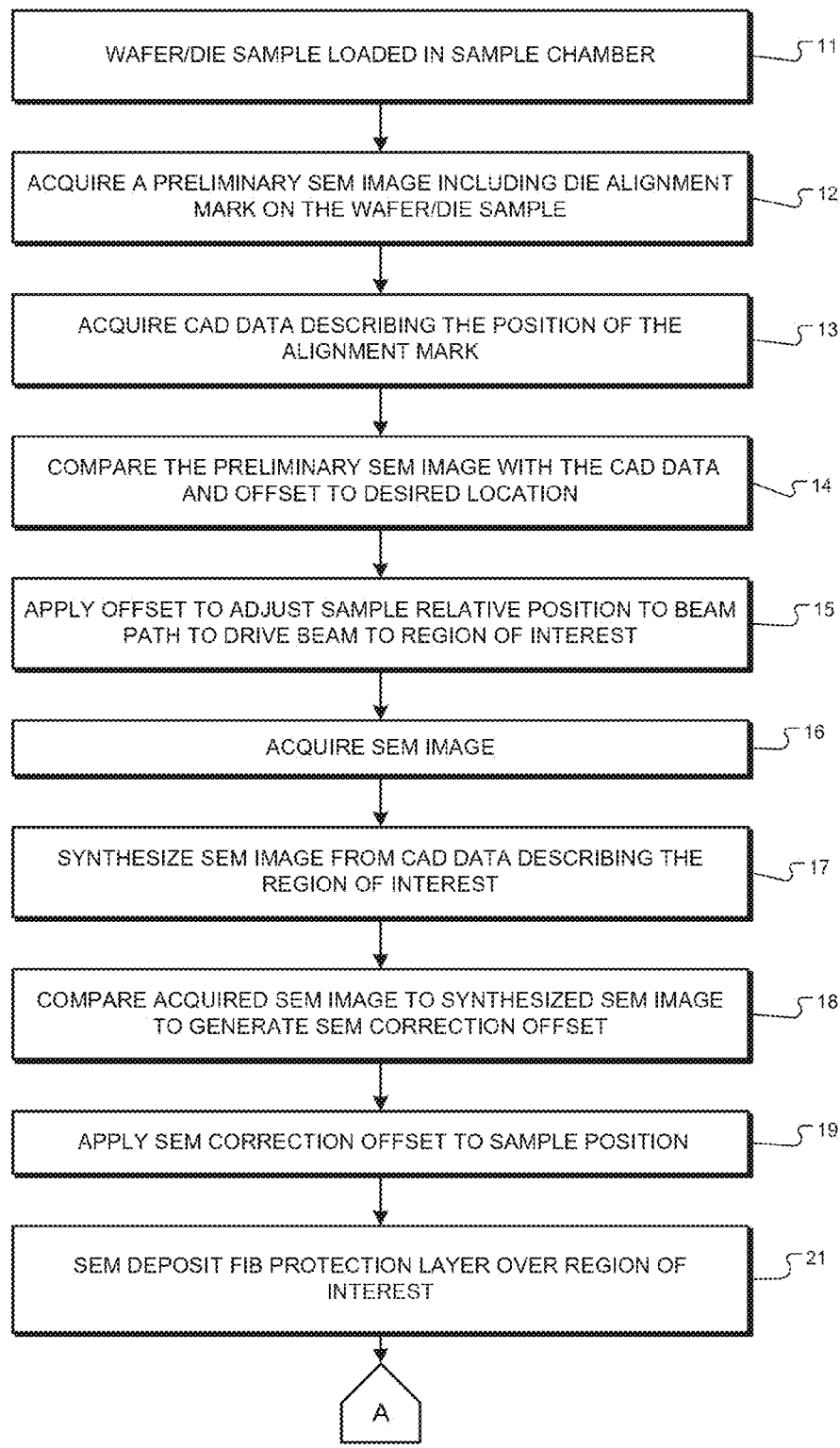
FIGS. 1A and 1B are a connected flow chart showing a method of automating a sample preparation recipe.
Figure 1B:
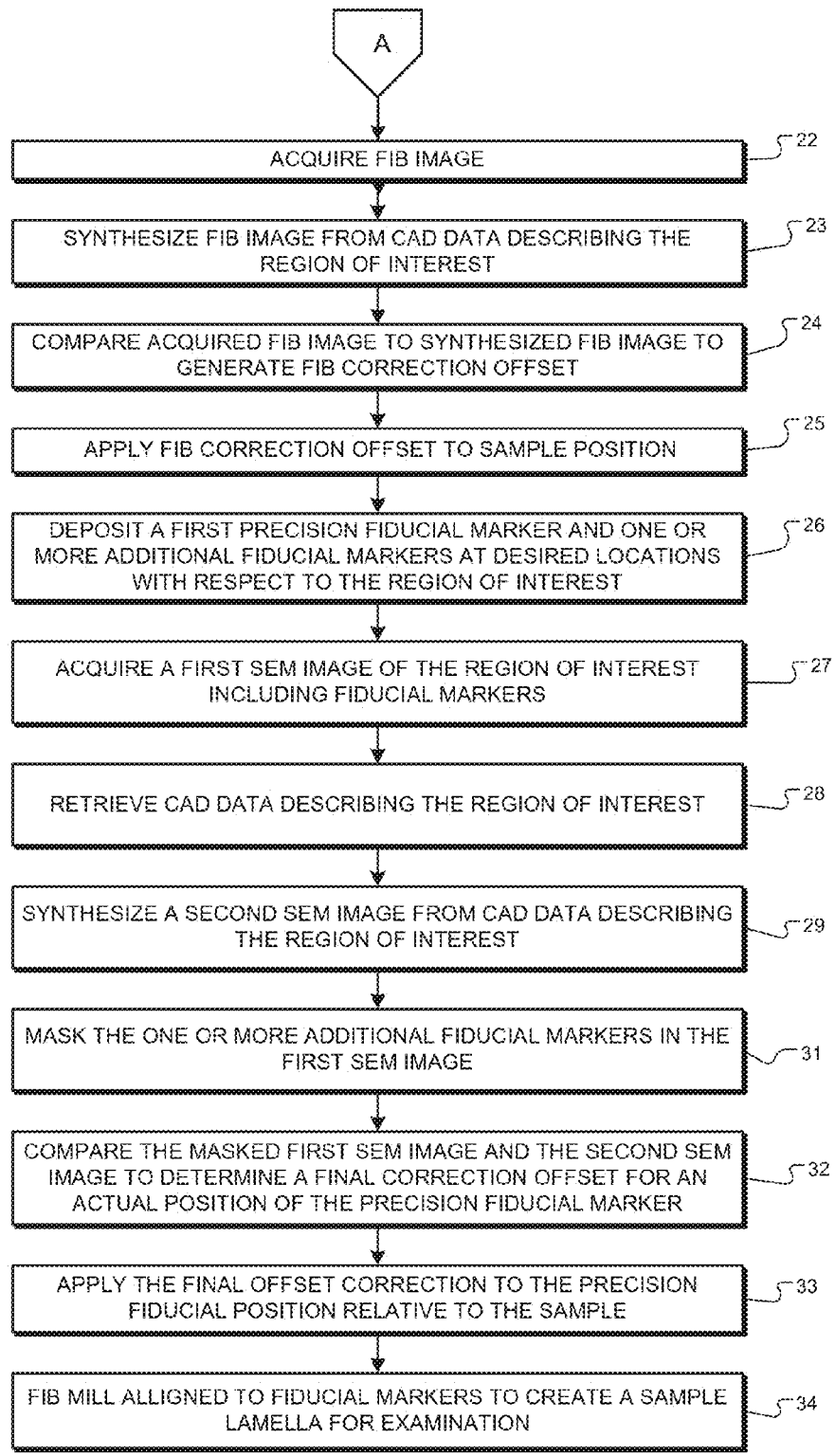

FIGS. 1A and 1B show a flowchart of a process for automating a recipe for creating a sample lamella according to one embodiment. In the preferred version, the depicted steps after loading the sample are fully automated in a dual-beam SEM/FIB system under control of a system controller and process controller such as those in the example system of FIG. 3. The system is preferably included in larger automated S/TEM sample management, such as the ExSolve system of FIG. 4, in which capability for machine-vision based metrology and image recognition, high-precision fiducial marks, and automatic fiducial placement are used to significantly improve lamella placement accuracy and precision. The techniques described herein may be integrated into the system of FIG. 4 to improve automation and accuracy of the lamella formation process, by providing a process to automatically align the SEM and FIB beams at the various automated recipe steps, so that fiducial and lamella creation takes place at a specified location.

The process begins at box 11 where a semiconductor wafer or portion thereof including one or more semiconductor dies is loaded into the sample chamber of the dual beam system. The semiconductor sample will have one or more regions of interest that are desired to be examined, for example to determine the presence or cause of process flaws or for quality control of critical features.

FIGS. 2A-J show a sequence of diagrams illustrating the example process of FIGS. 1A-1B. Referring to both sets of drawings, in FIG. 2A the depicted semiconductor wafer 201 loaded into the dual beam system at block 11 includes one or more semiconductor die 202, which are typically not yet separated into individual chips at this point, but may be. At block 12, the process acquires a preliminary SEM image at a first location or area 203 depicted enlarged as 204, the area including one or more die alignment marks 205 typically presented at the corners of die as shown in the enlarged view of the die corners. The beam may first be positioned using an optical imaging system or may be calibrated sufficiently that the process can go directly to acquiring the preliminary SEM image at the die desired to be examined.

Next at block 13 the process acquires CAD data describing a portion or snippet of the layout of the examined die, including the position of the alignment mark. This data may also include the position of the region of interest, but the location of that may already be provided by the process inputs. At block 14, the process next compares the preliminary SEM image 204 with the CAD data depicted by the overlaid image 206 (FIG. 2B) to determine whether the dual beam system, particularly the SEM beam, is correctly aligned with the die. Block 14 may first include processing the CAD data 206 to synthesize a SEM image suitable for direct comparison by known image feature alignment techniques. The images 204 and 206 are compared to determine whether there is an offset, shown by arrow 207, between where the system controller beam location tracking process has stored or "believes" the location of the SEM beam path to be relative to the die, and what it is actually measuring on the die. If an offset 207 is detected by the comparison, the system controller at block 15 applies the offset 207 by updating its stored position and orientation to reflect the more accurate known present position and orientation of the SEM device with respect to the die. The offset may include rotation as well. Preferably, the system at block 15 merely stores the correct position, and then proceeds to drive or move the beam path to place the beam at the desired location to examine the present region of interest. This may involve moving the sample stage or adjusting the beam position mechanically or with its beam steering control voltages.

Figure 2A:
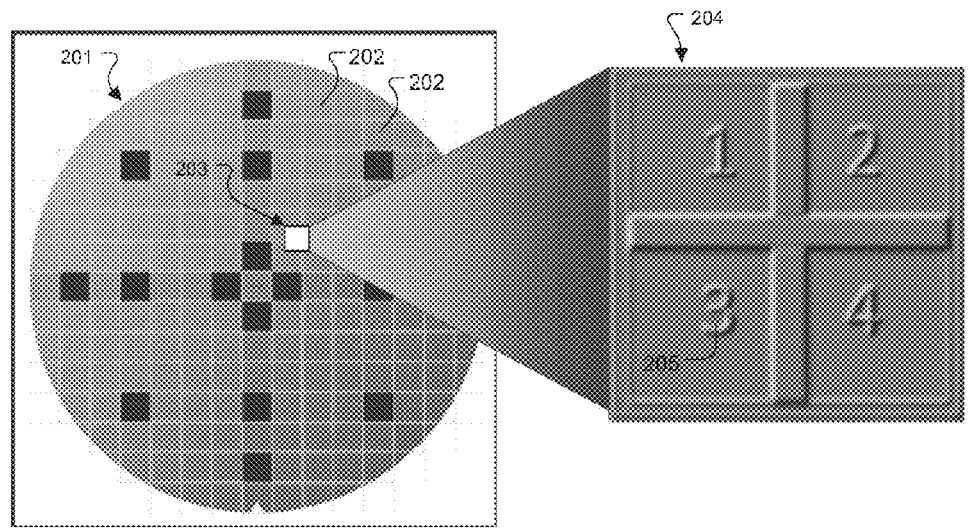
FIGS. 2A-J show a sequence of diagrams illustrating the example process of FIGS. 1A-1B.
Figure 2B:
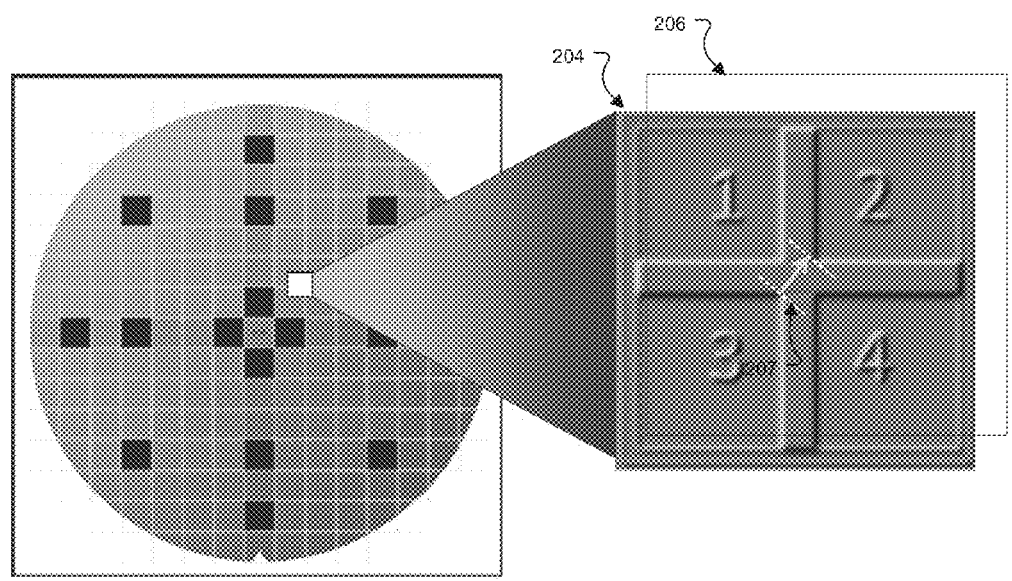
Figure 2C:
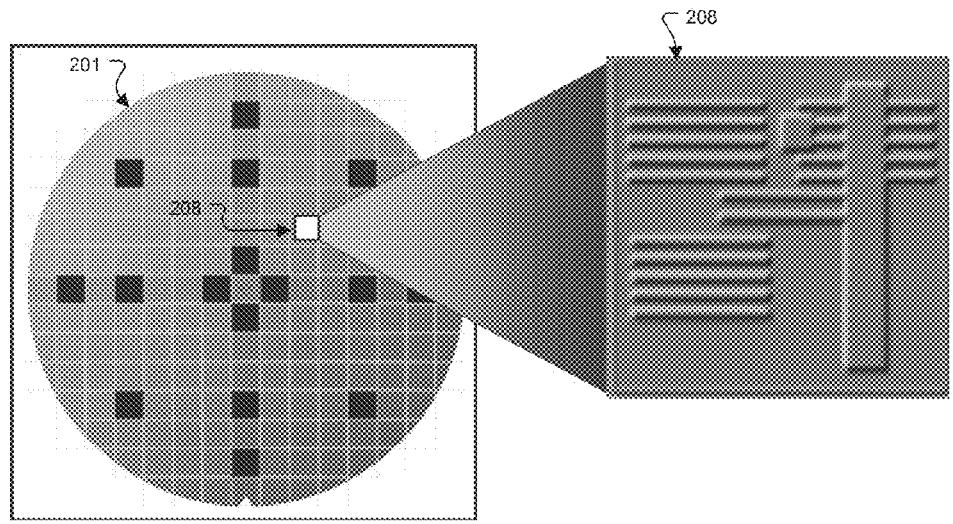
Figure 2D:
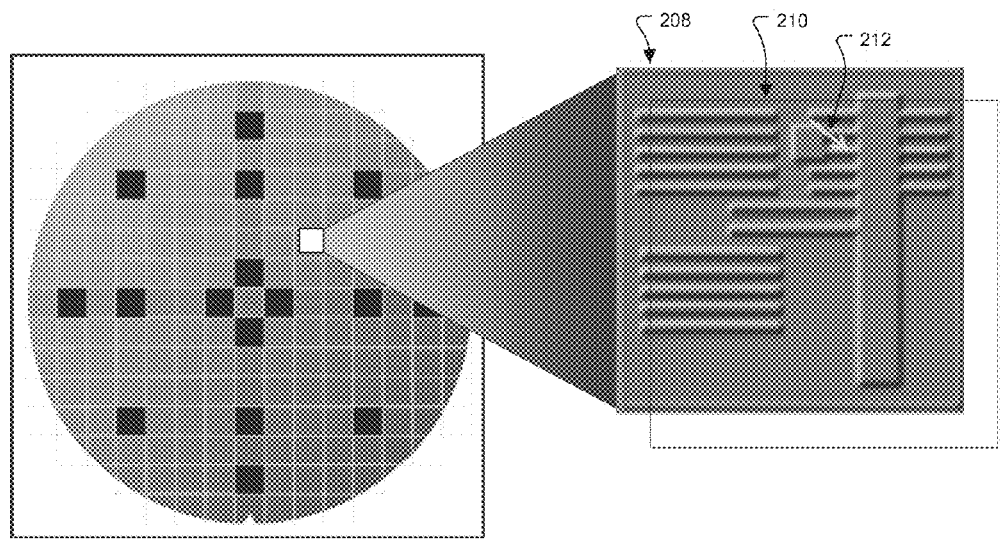

Next at block 16, the process acquires a SEM image 208 at the location of the region of interest, depicted as image 208 in FIG. 2C. While this embodiment uses an SEM, other versions may use an optical image or other particle beam image such as an FIB image. To determine that the beam is properly aligned at the location, the process next at block 17 acquires or recalls the CAD data describing the region of interest for comparison, and synthesizes from this CAD data an SEM image 210 suitable for comparison with the acquired image. The synthesized image 210 is preferably of the field of view expected from the acquired image, but may be larger to facilitate locating the actual area of the acquired image on the synthesized image. Generally the synthesis employs the dimensions of features defined in the CAD data, along with their defined materials, to model or approximate the SEM beam imaging process to create an image, typically luminance data in grayscale form. If an FIB image or optical image was used at block 16, the synthesis process at block 17 will synthesize an appropriate image for comparison. Next at block 18, the process compares the acquired SEM image to the synthesized image to determine whether there is any offset in alignment between the actual position of the SEM beam and the stored position where the system assumes the SEM image to have been acquired. This produces an offset distance and direction 212 to correct any offset of the beam from its desired location. The offset is applied in block 19, typically by updating the location of the beam to reflect the present actual location relative to the sample.

Figure 2E:
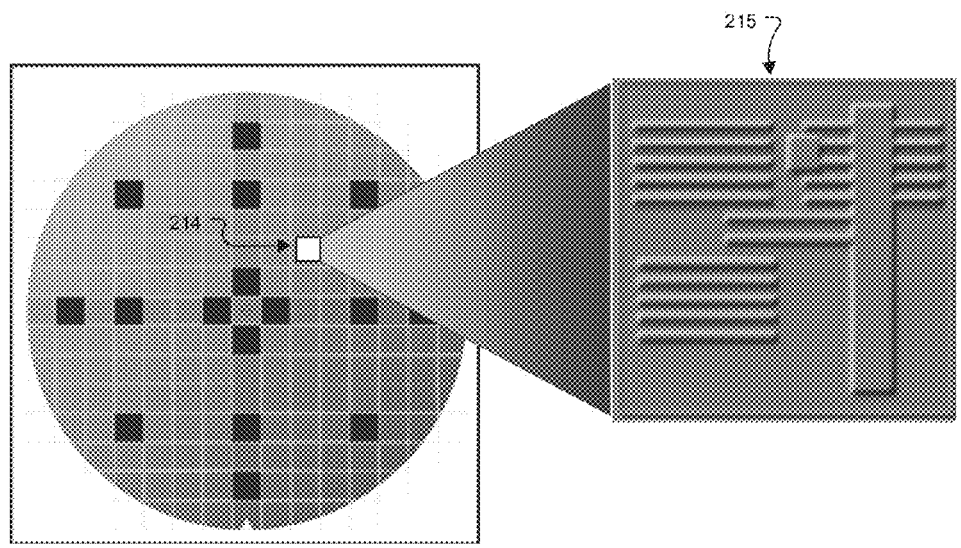
Figure 2F:
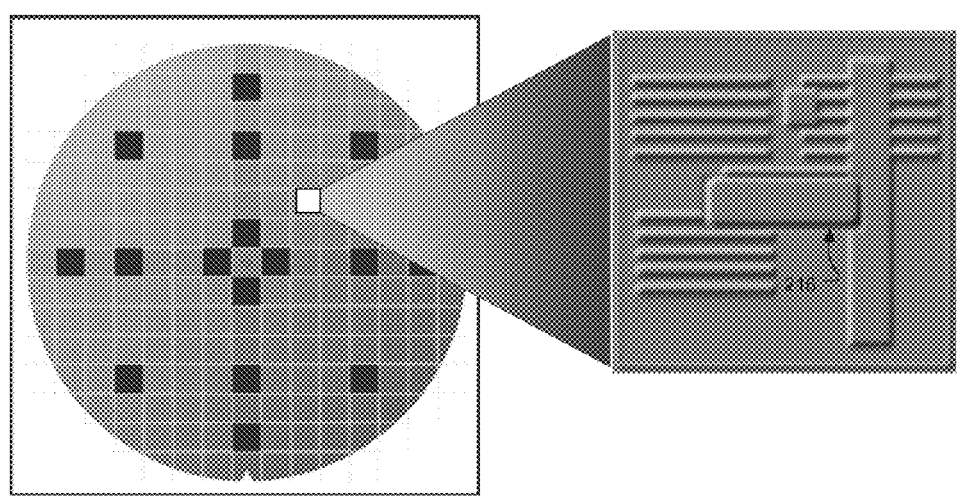
Figure 2G:
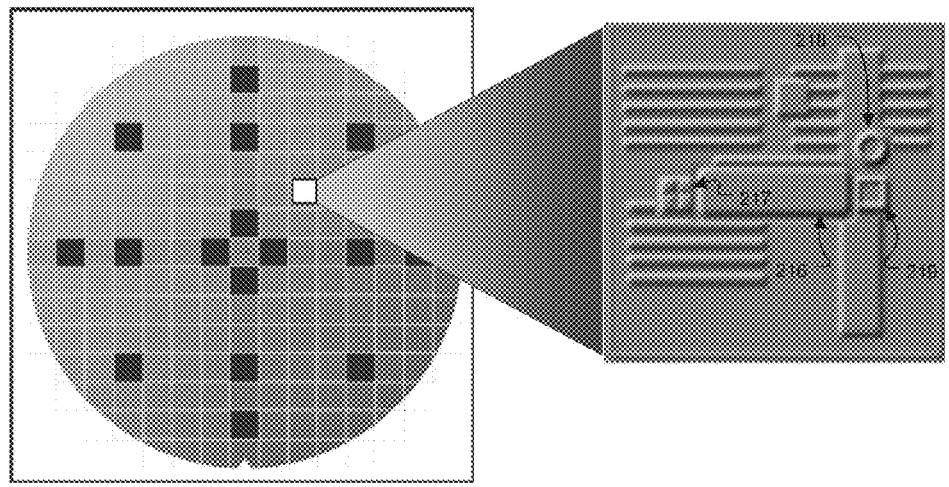

Next, the process at block 21 starts at the adjusted location, depicted as 214 in FIG. 2E, and performs an SEM deposition (electron beam induced deposition, EBID) of a protective layer 216 over the region of interest, to protect from damage or contamination from FIB deposition and milling that will be needed to complete the sample preparation. This deposition occurs according to known methods which typically employ one or more precursor gasses, such as Tungsten hexacarbonyl and Napthalene, acted upon by the scanned electron beam to deposit material, such as Tungsten or Carbon, respectively, on the surface of the sample. The protective layer 214 is preferably large enough to completely cover the surface of the sample volume that will be milled and removed as a lamella or other extracted sample such as a wedge or chunk.

Figure 1C:
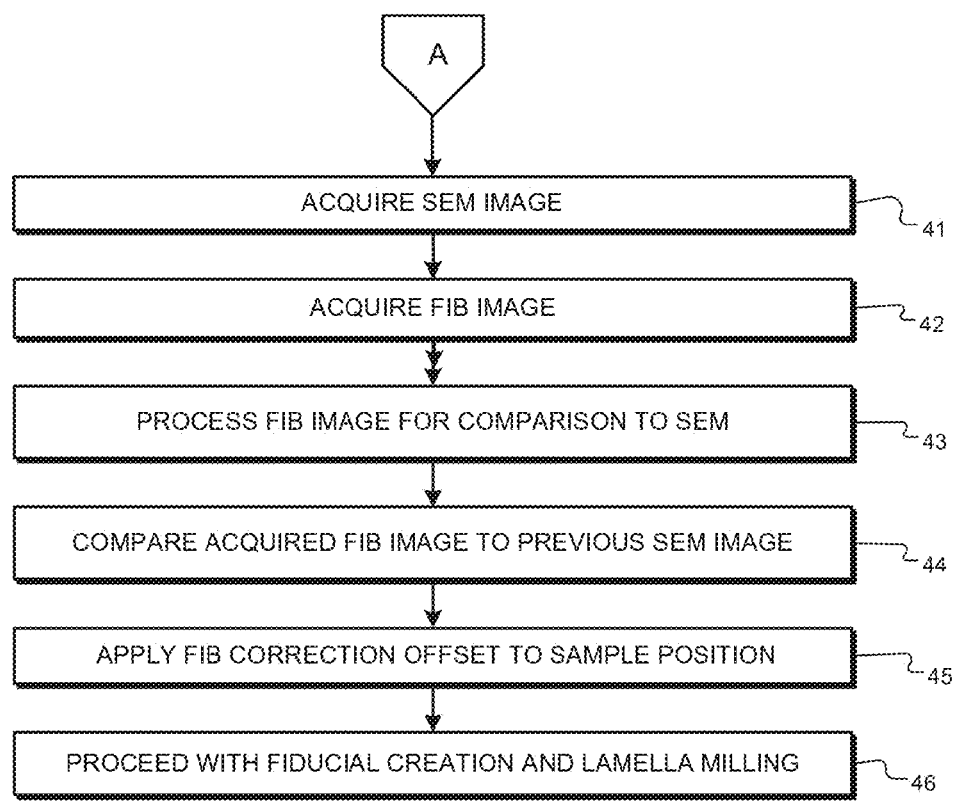
FIG. 1C is an alternative flowchart proceeding from FIG. 1A.

The flowchart continues at connector A in FIG. 1B. After depositing the protective layer with electron beam deposition, the process may align the focused ion beam to improve accuracy for the ion based deposition and milling that is to follow. Importantly, the FIB alignment may not always be in synch or known relative to the alignment of the SEM. FIG. 1B shows one automated alignment process for the FIB, while FIG. 1C shows another. The preferred process at block 22 acquires an FIB image of the region of interest. This image is formed according to known FIB imaging techniques, typically scanning the FIB at a lower beam current than the milling steps and detecting secondary electrons or secondary ions to form the image. Next at block 23, the process acquires CAD data for the region of interest in the FIB image, and synthesizes and FIB image for comparison to the acquired image. The synthesis of the FIB image includes selecting all the features in the CAD layout that are within the penetration range of the FIB, based upon the settings of the FIB as used to acquire the image. These features are layed-out or modeled and the layout created therefrom is modeled at each location (pixel) according to a material model indicating an expected emission amount (secondary electron emission) that the material has when exposed to a FIB at the current employed. These modeled emissions may be further filtered, transformed, or scaled to achieve the desired synthetic image. Next at block 24, the process compared the acquired FIB image with the synthesized FIB image to determine a location correction offset for the FIB. The correction offset is applied at block 25 to align the system controller's tracked location for the FIB with the actual location determined by the comparison. As with the SEM, this is preferably done by adjusting the tracked location in memory at the system controller, but may also be done with a movement of the beam or sample. With the FIB beam aligned, it can be driven to precise locations to create fiducials for aligning the lamella milling process. The fiducial locations are preferably specified automatically using CAD data to specify the location of the fiducial with respect to a particular structure on the wafer surface. This may be done in a pre-processing step associated with each particular feature to be examined. In other embodiments, automated FIB or SEM metrology can also be used to identify or help identify the lamella site, or to confirm that the site is correct. Such metrology may consist of image-based pattern recognition, edge finding, ADR, center-of-mass calculations, blobs, etc.

Next, at block 26, the process use focused ion beam (FIB) induced deposition to deposit a first precision fiducial marker and one or more additional fiducial markers at desired locations with respect to the region of interest. Preferably, a combination of high precision (fine) fiducials and low precision (bulk) fiducials are used to optimize lamella placement precision and accuracy, as described, for example, in U.S. Pat. No. 8,134,124, for "Method for Creating S/TEM Sample and Sample Structure" to Blackwood et al, which is assigned to the assignee of the present application and which is hereby incorporated by reference. In the preferred fiducial arrangement shown in FIG. 2G, the high-precision fiducial 219 is created at one end of the region of interest, and two additional fiducials 217 and 218, which may be low-precision fiducial marks or a mixture of the different types, are located at either end of the region of interest. This is not limiting and any suitable number and shape of high-precision and low-precision fiducials may be employed. The drawing is not exactly to scale and typically low-precision fiducials will be larger to facilitate location on lower resolution scanned images for rough milling when the lamella milling process is conducted. These low-precision fiducials are used for gross-structure pattern recognition, such as quickly re-finding the approximate lamella location and determining the location for bulk milling of the lamella. Because a larger beam size will be used for the bulk milling, a suitable low precision fiducial should be easily identified by pattern recognition software even in lower resolution images.

With the fiducials created, the process now prepares to mill out the sample lamella from the region of interest. To best do so, it must determine the precise location at which the high-precision fiducial has actually been deposited, versus the desired target location, which may not be the same because of sample drift or other alignment problems that may occur during FIB deposition. To determine this actual location, the process first acquires a SEM image including the region of interest and the fiducials at block 27. Next, the process retrieves CAD data describing the same area for comparison at block 28. Then the process synthesizes another SEM image 222 (FIG. 2i) from the CAD data, using SEM synthesis techniques as discussed above.

Figure 2H:
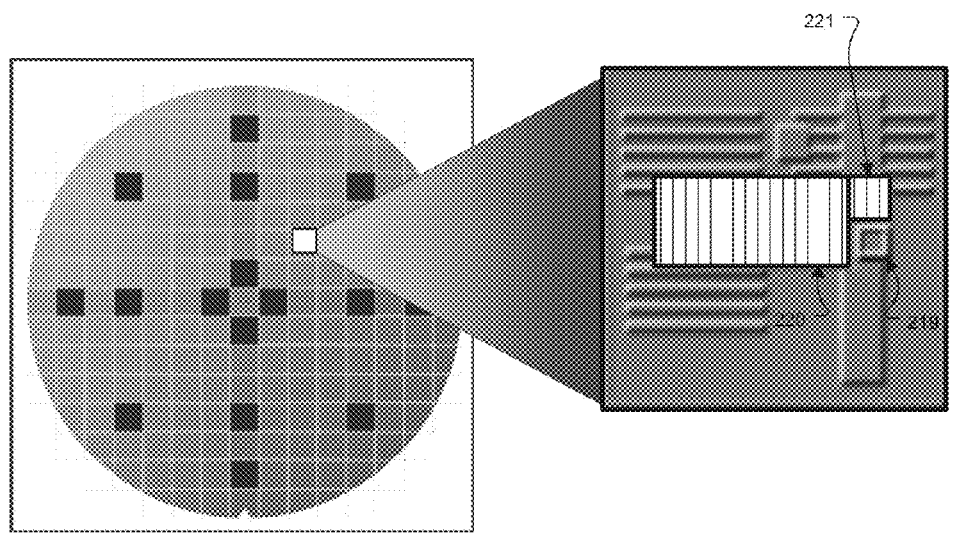
Figure 2I:
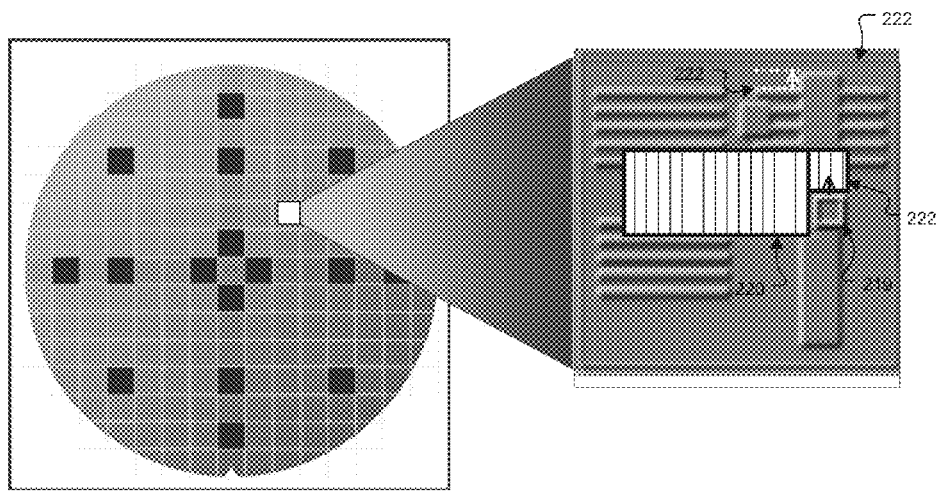
Figure 2J:
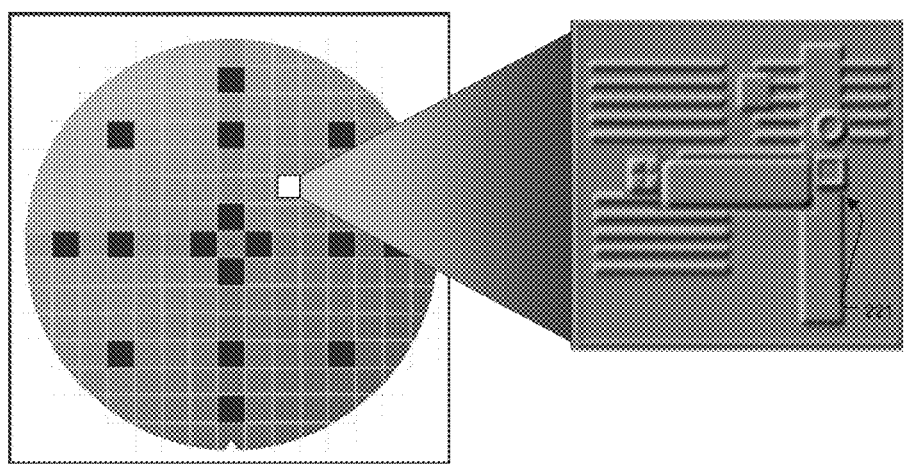

To compare the synthesized image with the acquired image, the process at block 31 first masks the one or more additional fiducial markers 217 and 218 in the acquired SEM image, so that they will not interfere with the image comparison, while leaving the high-precision fiducial 219 unmasked as depicted in FIG. 2H. For versions that use an SEM deposition to provide a protective layer (like that done in this embodiment at block 21), the masking also includes masking off the protective layer deposit 216. The masking preferably eliminates the image portions including shapes of the deposited structures from the image in some manner so they do not introduce errors into the image comparison, with example 'masking' shown by the blanked-out areas 220 and 221 depicted in FIG. 2H. For example, the image data may be removed from the image, or a label or other instruction may be created for input to the image comparison process at block 32 causing the process to ignore data from the masked regions during the comparison. The masked data may also be nulled out or replaced with the average luminance value of the entire image. The masked areas 220 and 221 may be located for masking by searching the images for the fiducial marks, with the FIB protection layer 216 located from its location relative to the surrounding fiducials. Or the masked features may be located simply by masking off their best known locations, which may include masking off a larger area than their known sizes to account for possible location errors. With the masking created at block 31, the process at block 32 compares the masked SEM image and the synthesized SEM image to determine a final correction offset such as the depicted offset 222 for determining an actual position of the precision fiducial marker. Next at block 33, the process applies the final offset correction such as to a stored actual location of the precision fiducial marker, again preferably applying the offset to the location of the precision fiducial relative to the sample, but optionally using other methods of applying the offset. Next at block 34, the process, with reference to the corrected location the precision fiducial marker, mills with the FIB to create a sample lamellae for examination. The lamella milling may be conducted with suitable known techniques that automatically mill a lamella of desired size and shape with reference to a local precision fiducial. These techniques typically include rough milling steps (relatively large beam) that reference the position of the low precision fiducials, and fine milling steps that reference the position of the high-precision fiducial.

The above-described embodiment provides a manner to automatically and accurately create lamellas or other sample portions from a wafer, preferably without human intervention as each step can be automatically controlled. It is noted that while the process steps in the depicted process go in order for the creation of a single lamella, in actuality the process is typically applied to create multiple lamellas on a sample wafer, and therefore the steps in the process may be applied to multiple locations, and the process for any particular lamella formation may be interrupted to conduct similar steps at other locations. In some versions, the SEM protective layers are deposited at all locations, then the fiducials are formed at all locations, then the lamella milling is conducted at all locations. In some scenarios, the automated beam alignment steps discussed above may be sufficient to keep the beam aligned for multiple locations. For example, aligning the FIB beam position may be done once, and then fiducials created at all desired locations. Or, the beam alignment procedure may be done periodically for processing larger numbers of locations, without requiring automatic beam alignment at every location.

FIG. 1C is a flowchart showing an alternative method of calibrating the FIB beam from that found in FIG. 2B. The depicted method begins at connector A from FIG. 2A. Before the fiducials can be formed, the location shift from the SEM beam location to the FIB location must be corrected so that the system controller tracks the actual location of the FIB for deposition and milling. The process of FIG. 1B performs such calibration by acquiring FIB image and aligning it with a synthesized FIB image. In this version, the FIB location is compared to the already-calibrated SEM beam location by comparing an image acquired with each beam. An SEM image is acquired at block 41, which may be done at the region of interest or another suitable area nearby. Next at block 42, the process acquires an FIB image of the same area. At block 43, the acquired FIB image may optionally be processed to make its luminance properties more similar to an SEM image for comparison. Next at block 44, the process compares the two images to determine the offset distance and direction between them. Next, at block 45, the process applies this location correction offset to the FIB tracked location. With the FIB now aligned, the process continues with the fiducial creation and lamella milling as described with respect to FIG. 1B steps 26-34.

Figure 3:
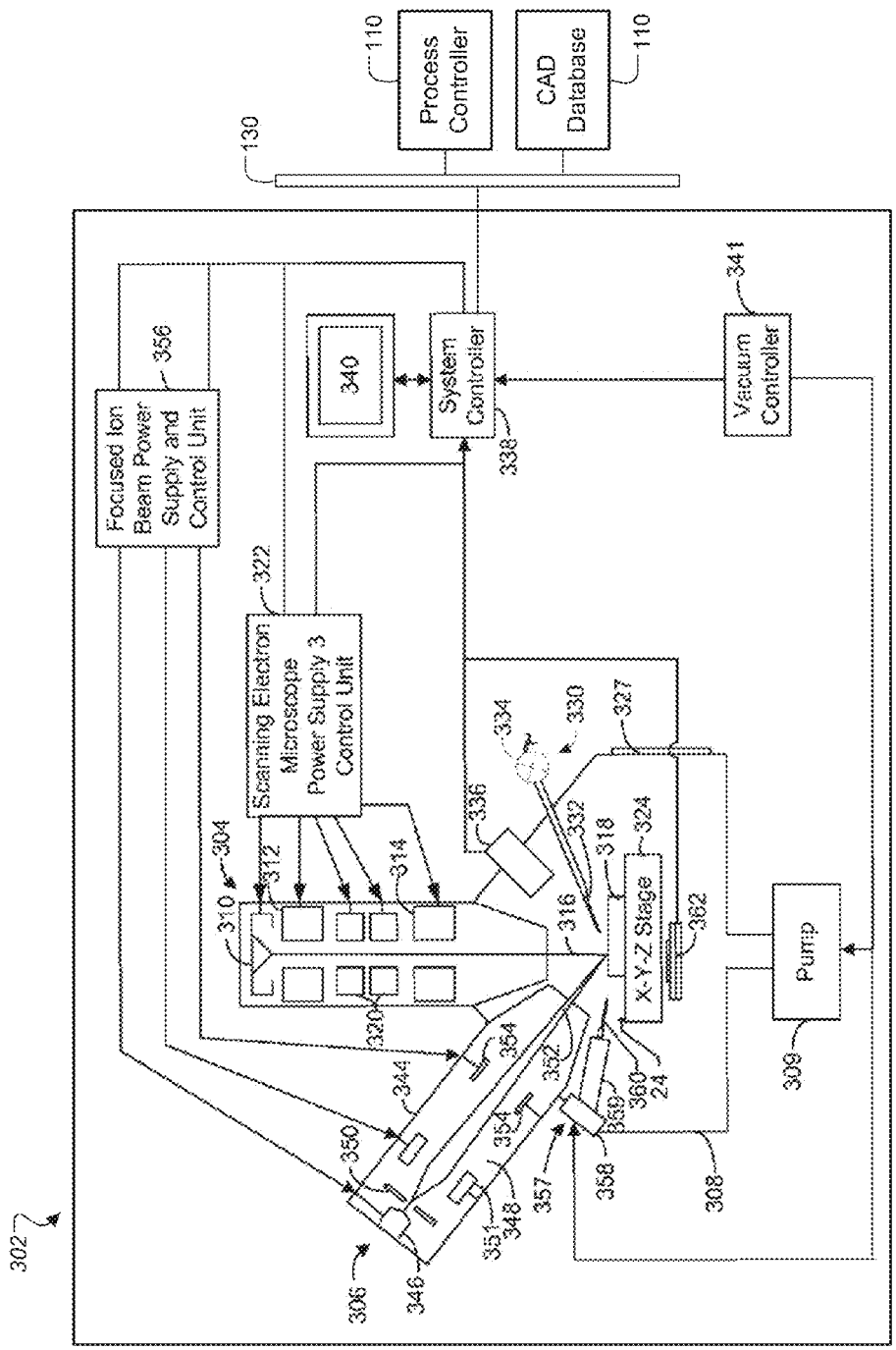
FIG. 3 is a schematic view of a dual beam system employed according to some embodiments of the invention.
Figure 4:
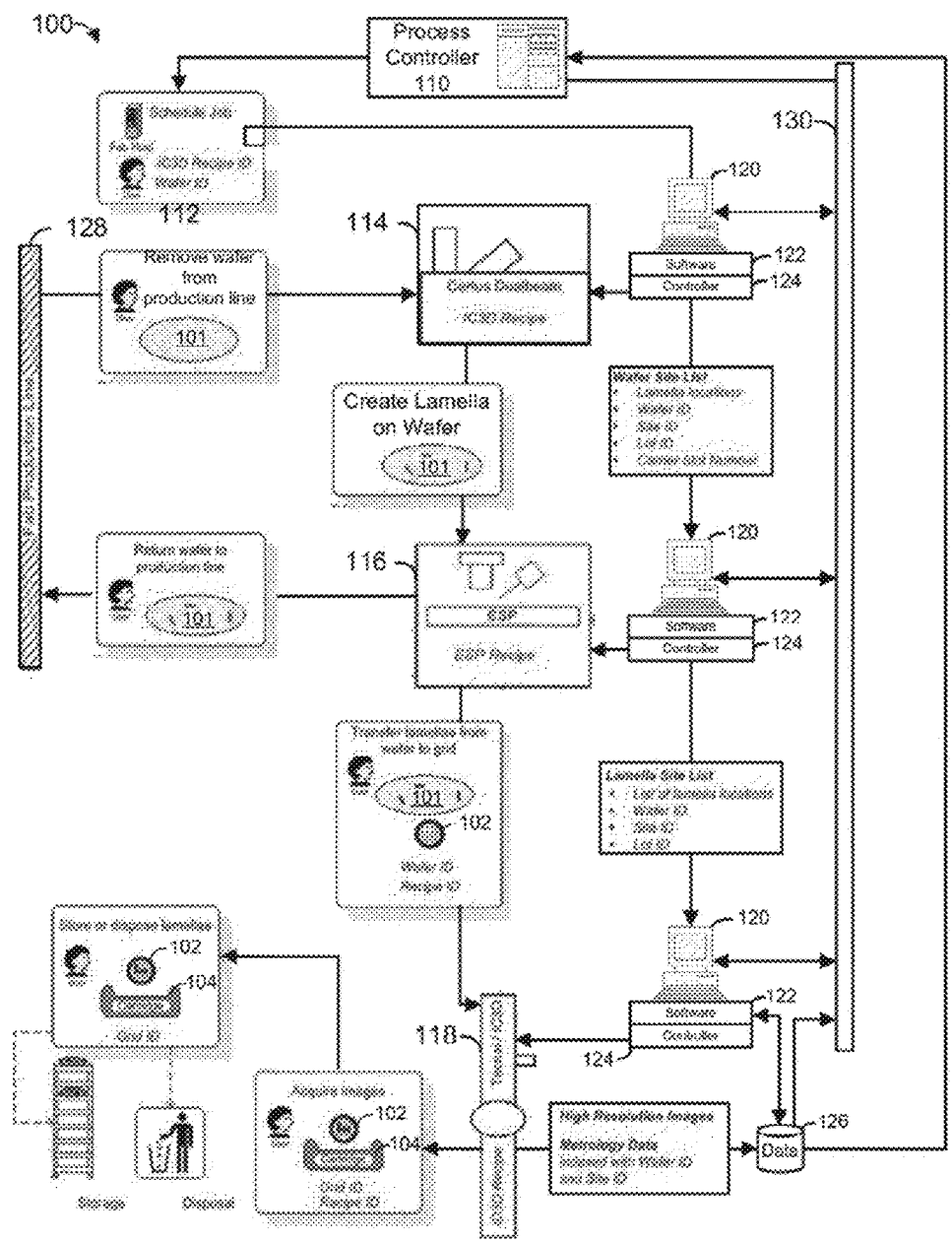
FIG. 4 illustrates a prior art automated S/TEM sample management (available commercially the ExSolve system) into which the dual-beam system and the system and controller processes described herein may be integrated to improve automation.

FIG. 3 is a schematic diagram of a one embodiment of an exemplary dual beam SEM/FIB system 302 that is equipped to carry out a method according to the present invention. As discussed above, embodiments of the present invention can be used in a wide variety of applications. Suitable dual beam systems are commercially available, for example, from FEI Company, Hillsboro, Oreg., the assignee of the present application. While an example of suitable hardware is provided below, the invention is not limited to being implemented in any particular type of dual beam device. The system controller 338 controls the operations of the various parts of dual beam system 302. Through system controller 338, a user can cause ion beam 352 or electron beam 316 to be scanned in a desired manner through commands entered into a conventional user interface (not shown). In the preferred embodiments herein, system controller 338 controls dual beam system 302 to perform the techniques discussed herein automatically in accordance with programmed instructions, some of which may be issued by the process controller 110, connected to network 130. CAD database 110 is also operatively connected to dual beam system 302 and process controller 110 over network 130. The CAD database 110 may be provided on a system computer such as a Fab Host Controller 112 (FIG. 4), a dedicated CAD database computer, or the process controller 110. What is important is the CAD database is available to supply requested layouts to the system controller to conduct the automated processes described above.

Dual beam system 302 has a vertically mounted electron beam column 304 and a focused ion beam (FIB) column 306 mounted at an angle of approximately 52 degrees from the vertical on an evacuable specimen chamber 308. The specimen chamber may be evacuated by pump system 309, which typically includes one or more, or a combination of, a turbo-molecular pump, oil diffusion pumps, ion getter pumps, scroll pumps, or other known pumping means.

The electron beam column 304 includes an electron source 310, such as a Schottky emitter or a cold field emitter, for producing electrons, and electron-optical lenses 312 and 314 forming a finely focused beam of electrons 316. Electron source 310 is typically maintained at an electrical potential of between 500 V and 30 kV above the electrical potential of a work piece 318, which is typically maintained at ground potential.

Thus, electrons impact the work piece 318 at landing energies of approximately 500 eV to 30 keV. A negative electrical potential can be applied to the work piece to reduce the landing energy of the electrons, which reduces the interaction volume of the electrons with the work piece surface, thereby reducing the size of the nucleation site. Work piece 318 may comprise, for example, a semiconductor device, micro-electromechanical system (MEMS), or a lithography mask. The impact point of the beam of electrons 316 can be positioned on and scanned over the surface of a work piece 318 by means of deflection coils 320. Operation of lenses 312 and 314 and deflection coils 320 is controlled by scanning electron microscope power supply and control unit 322. Lenses and deflection unit may use electric fields, magnetic fields, or a combination thereof.

Work piece 318 is on movable stage 324 within specimen chamber 308. Stage 324 can preferably move in a horizontal plane (X and Y axes) and vertically (Z axis) and can tilt approximately sixty (60) degrees and rotate about the Z axis.

A door 327 can be opened for inserting work piece 318 onto X-Y-Z stage 324 and also for servicing an internal gas supply reservoir (not shown), if one is used. The door is interlocked so that it cannot be opened if specimen chamber 308 is evacuated.

Mounted on the vacuum chamber are multiple gas injection systems (GIS) 330 (two shown). Each GIS comprises a reservoir (not shown) for holding the precursor or activation materials and a needle 332 for directing the gas to the surface of the work piece. Each GIS further comprises means 334 for regulating the supply of precursor material to the work piece. In this example the regulating means are depicted as an adjustable valve, but the regulating means could also comprise, for example, a regulated heater for heating the precursor material to control its vapor pressure.

When the electrons in the electron beam 316 strike work piece 318, secondary electrons, backscattered electrons, and Auger electrons are emitted and can be detected to form an image or to determine information about the work piece. Secondary electrons, for example, are detected by secondary electron detector 336, such as an Everhart-Thornley detector, or a semiconductor detector device capable of detecting low energy electrons. STEM detector 362, located beneath the TEM sample holder 318 and the stage 324, can collect electrons that are transmitted through a sample 318 mounted on the TEM sample holder 318. Signals from the detectors 336, 362 are provided to a system controller 338. Said controller 338 also controls the deflector signals, lenses, electron source, GIS, stage and pump, and other items of the instrument. Monitor 340 is used to display user controls and an image of the work piece using the signal The chamber 308 is evacuated by pump system 309 under the control of vacuum controller 341. The vacuum system provides within chamber 308 a vacuum of approximately $3 \times 10^{-6}$ mbar. When a suitable precursor or activator gas is introduced onto the sample surface, the chamber background pressure may rise, typically to about $5 \times 10^{-5}$ mbar.

Focused ion beam column 306 comprises an upper neck portion 344 within which are located an ion source 346 and a focusing column 348 including extractor electrode 350 and an electrostatic optical system including an objective lens 351. Ion source 346 may comprise a liquid metal gallium ion source, a plasma ion source, a liquid metal alloy source, or any other type of ion source. The axis of focusing column 348 is tilted 52 degrees from the axis of the electron column. An ion beam 352 passes from ion source 346 through focusing column 348 and between electrostatic deflectors 354 toward work piece 318.

FIB power supply and control unit 356 provides an electrical potential at ion source 346. Ion source 346 is typically maintained at an electrical potential of between 1 kV and 60 kV above the electrical potential of the work piece, which is typically maintained at ground potential. Thus, ions impact the work piece at landing energies of approximately 1 keV to 60 keV. FIB power supply and control unit 356 is coupled to deflection plates 354 which can cause the ion beam to trace out a corresponding pattern on the upper surface of work piece 318. In some systems, the deflection plates are placed before the final lens, as is well known in the art. Beam blanking electrodes (not shown) within ion beam focusing column 348 cause ion beam 352 to impact onto blanking aperture (not shown) instead of work piece 318 when a FIB power supply and control unit 356 applies a blanking voltage to the blanking electrode.

The ion source 346 typically provides a beam of singly charged positive gallium ions that can be focused into a sub one-tenth micrometer wide beam at work piece 318 for modifying the work piece 318 by ion milling, enhanced etch, material deposition, or for imaging the work piece 318.

A micromanipulator 357, such as the AutoProbe200™ from Omniprobe, Inc., Dallas, Tex., or the Model MM3A from Kleindiek Nanotechnik, Reutlingen, Germany, can precisely move objects within the vacuum chamber. Micromanipulator 357 may comprise precision electric motors 358 positioned outside the vacuum chamber to provide X, Y, Z, and theta control of a portion 359 positioned within the vacuum chamber. The micromanipulator 357 can be fitted with different end effectors for manipulating small objects. In the embodiments described herein, the end effector is a thin probe 360. As is known in the prior art, a micromanipulator (or microprobe) can be used to transfer a TEM sample (which has been freed from a substrate, typically by an ion beam) to a TEM sample holder 318 for analysis.

It should be noted that FIG. 3 is a schematic representation, which does not include all the elements of a typical dual beam system for the sake of simplicity, and which does not reflect the actual appearance and size of, or the relationship between, all the elements.

One suitable S/TEM sample management tool suite in which the present invention may be employed is described in U.S. Pat. No. 8,890,064 to Arjavac et al., which is commonly owned by the assignee of the present invention, and is hereby incorporated by reference. The sample management suite generally includes a Process Controller and a Fab Host computer operably connected to (or integrated with) a dual-beam or FIB system for creating lamella, a lamella extraction tool, and a S/TEM system for examining the lamella. Integrating the present system with the prior art tool suite involves installing the improved dual beam system as described herein, with programming to provide the automated workflow. The process controller may also be programmed to specify defect locations and desired lamella sizes and orientations for each defect or region of interest to be studied. The process host or other machine may need programming adjustments so that it can provide detailed CAD data responsive to requests from the dual beam system controller at the various steps described herein. However, some existing systems already include a CAD database operatively connected to the network and able to respond to requests to provide specified CAD data. The system controller or process controller may further be programmed to synthesize FIB images as described herein.

While the automated workflow processes described above focus on the beam alignment and automated lamella creation, the recipe for the defect review process may further include some or all of the following parameters for a scanning electron microscope (SEM) defect review tool as described in the incorporated U.S. Pat. No. 8,890,064: Wafer Rotation (if applicable); Wafer alignment points (optical and electron beam); add/remove test dies; Wafer Tilt (if applicable); SEM Column—Landing Energy; SEM Column—current; SEM Column—extraction current; Automatic Defect Locator (ADL) parameters such as video levels, focusing parameters, initial field of view (FOV); FOV; Acquisition times or frames; Automatic Defect Classification (ADC); Auto-focus; Charge Control; Contrast and brightness settings (if applicable); and Defect sampling. Each of these different parameters may be determined from the inspection results as described above. Obviously, the parameters that are included in the recipe may vary depending on, for example, the configuration of the defect review tool. For instance, the above listed parameters may be suitable for an electron beam-based defect review tool, and a recipe for a different type of defect review tool (e.g., a high resolution optical imaging system) may include a different set of parameters.

Although the present invention and its advantages have been described in detail, it should be understood that various changes, substitutions and alterations can be made herein without departing from the spirit and scope of the invention as defined by the appended claims. The combinations of features described herein should not be interpreted to be limiting, and the features herein may be used in any working combination or sub-combination according to the invention. Further, the various novel workflow processes herein may be employed to improve prior art workflows, such as the processes described in the incorporated patent, and the description should be interpreted as supporting such an incorporation where fiducial location needs to be verified in a workflow, or where the SEM or FIB beam alignment needs to be verified. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for automatically preparing a semiconductor sample in a dual-beam charged particle system, the method comprising:
   positioning the dual-beam charged particle system with respect to a semiconductor die sample region of interest to be examined in a sample chamber;
   with focused ion beam (FIB) deposition, forming a first precision fiducial marker and one or more additional fiducial markers at desired locations with respect to the region of interest;
   acquiring a first scanning electronic microscope (SEM) image of the region of interest;
   retrieving computer aided design (CAD) data describing the region of interest;
   synthesizing a second SEM image from CAD data describing the region of interest;
   masking the one or more additional fiducial markers in the first SEM image and comparing the masked first SEM image and the second SEM image to determine a final correction offset for an actual position of the precision fiducial marker;
   applying the final correction offset to the location of the precision fiducial marker;
   based on the corrected location of the precision fiducial marker, adjusting the position of the FIB relative to the sample, and milling with the FIB to create a sample lamellae for examination.

2. The method of claim 1, wherein positioning the dual-beam charged particle system includes aligning with a desired field of view by comparing CAD data to an acquired image.

3. The method of claim 2, wherein aligning with a desired field of view comprises
(a) acquiring a preliminary SEM image including an alignment mark on the semiconductor die sample;
(b) acquiring CAD data describing the position of the alignment mark;
(c) comparing the preliminary SEM image with the CAD data and determining an first alignment correction offset; and
(d) based on the first alignment correction offset, adjusting the sample position relative to the position of the beam paths of the dual-beam system to direct the beam paths toward the region of interest.

4. The method of claim 1, further comprising, before FIB deposition of the fiducial markers,
(a) acquiring a FIB image from the FIB device;
(b) synthesizing a FIB image from the CAD data describing the region of interest;
(c) comparing the acquired FIB image to the synthesized FIB image to generate a FIB correction offset; and
(d) applying the FIB correction offset to the sample position.

5. The method of claim 1, further comprising, before FIB deposition of the fiducial markers, aligning the FIB beam by comparing an acquired SEM image to an acquired FIB image, and updating a tracked location for the FIB beam based on the results of the comparison.

6. The method of claim 1, further comprising, before the FIB deposition, depositing a protective layer over at least a portion of the region of interest.

7. The method of claim 6, wherein the protective layer is deposited by electron beam-induced deposition (EBID).

8. The method of claim 7, wherein depositing the protective layer with EBID further includes
(a) after positioning the dual beam charged particle system, acquiring an SEM image of the field of view;
(b) acquiring CAD data describing the position of the die sample region of interest;
(c) synthesizing a SEM image from the acquired CAD data;
(d) comparing the acquired SEM image to the synthesized SEM image to determine an SEM alignment correction offset;
(e) applying the SEM alignment correction offset to the FIB position; and
(f) then depositing the protective layer with EBID.

9. The method of claim 6, further comprising, when masking the one or more additional fiducial markers, also masking the protective layer.

10. A method for automatically preparing a semiconductor sample in a dual-beam charged particle system, the method comprising:
aligning a scanning electron microscope (SEM) beam the dual-beam charged particle system with a desired feature of interest on a sample in a sample chamber by comparing computer aided design (CAD) data to an acquired SEM image and applying a resulting SEM correction offset;
then, with beam-induced deposition, depositing a protective layer over at least part of the region of interest;
then, with a focused ion beam (FIB), creating a first precision fiducial marker and one or more additional fiducial markers at desired locations with respect to the region of interest;
acquiring a scanning electronic microscope (SEM) image of the region of interest;
retrieving CAD data describing the region of interest;
synthesizing a second SEM image from CAD data describing the region of interest;
masking the one or more additional fiducial markers and the protective layer in the first SEM image and comparing the masked first SEM image and the second SEM image to determine a final correction offset for an actual position of the precision fiducial marker;
applying the final correction offset to the FIB position and then FIB milling with reference to the corrected position to create a sample lamellae for examination.

11. The method of claim 10, further comprising, before creating the fiducial markers, acquiring a FIB image from the FIB device; synthesizing a FIB image from the CAD data describing the region of interest; comparing the acquired FIB image to the synthesized FIB image to generate a FIB correction offset; applying the FIB correction offset to the FIB position relative to the sample.

12. An automated sample preparation system comprising:
a dual-beam scanning and milling system including a scanning electron microscope (SEM), a focused ion beam (FIB) both pointing at a sample chamber, a system controller operatively connected to the SEM and FIB and including at least one processor and tangible non-transitory computer media storing program instructions executable by the at least one processor for:
aligning a scanning electron microscope (SEM) beam the dual-beam charged particle system with a desired feature of interest on a sample in the sample chamber by comparing computer aided design (CAD) data to an acquired SEM image and applying a resulting SEM correction offset;
then, with beam-induced deposition, depositing a protective layer over at least part of the region of interest;
then, with a focused ion beam (FIB), creating a first precision fiducial marker and one or more additional fiducial markers at desired locations with respect to the region of interest;
acquiring a scanning electronic microscope (SEM) image of the region of interest;
retrieving CAD data describing the region of interest;
synthesizing a second SEM image from CAD data describing the region of interest;
masking the one or more additional fiducial markers and the protective layer in the first SEM image and comparing the masked first SEM image and the second SEM image to determine a final correction offset for an actual position of the precision fiducial marker;
applying the final correction offset to the FIB position and then FIB milling with reference to the corrected position to create a sample lamellae for examination.

13. The system of claim 12, wherein the program instructions are further executable for, before FIB deposition of the fiducial markers,
(a) acquiring a FIB image from the FIB device;
(b) synthesizing a FIB image from the CAD data describing the region of interest;
(c) comparing the acquired FIB image to the synthesized FIB image to generate a FIB correction offset; and (d) applying the FIB correction offset to the sample position.

14. The system of claim 12, wherein the program instructions are further executable for, before FIB deposition of the fiducial markers, aligning the FIB beam by comparing an acquired SEM image to an acquired FIB image, and updating a tracked location for the FIB beam based on the results of the comparison.

15. The system of claim 12, further comprising:
a plucker device operable to remove one or more lamellas from the sample;
a transmission electron microscope (TEM), operable to receive the one or more lamellas from the plucker device and conduct scans;
a process controller operatively connected to the dual beam scanning and milling system, the plucker device, and the TEM and operable to command them to execute functions in an automated workflow.

* * * * *